US006224887B1

(12) United States Patent
Samour et al.

(10) Patent No.: US 6,224,887 B1
(45) Date of Patent: May 1, 2001

(54) ANTIFUNGAL NAIL LACQUER AND METHOD USING SAME

(75) Inventors: Carlos M. Samour, Bedford; Scott F. Krauser, Tyngsboro, both of MA (US)

(73) Assignee: MacroChem Corporation, Lexington, MA (US)

( * ) Notice: Subject to any disclaimer, the term of this patent is extended or adjusted under 35 U.S.C. 154(b) by 0 days.

(21) Appl. No.: 09/245,714

(22) Filed: Feb. 8, 1999

Related U.S. Application Data

(60) Provisional application No. 60/074,025, filed on Feb. 9, 1998.

(51) Int. Cl.[7] .............................. A61K 6/00; A61K 7/00; A61K 7/04; A01N 25/34

(52) U.S. Cl. ............................ 424/401; 424/61; 424/404

(58) Field of Search .............................. 424/61, 401, 404

(56) References Cited

U.S. PATENT DOCUMENTS

| | | | | |
|---|---|---|---|---|
| 4,636,520 | | 1/1987 | Umio et al. | 514/399 |
| 4,957,730 | | 9/1990 | Bohn et al. | 424/61 |
| 5,002,938 | | 3/1991 | Wang et al. | 514/171 |
| 5,110,809 | | 5/1992 | Wang et al. | 514/171 |
| 5,120,530 | | 6/1992 | Ferro et al. | 424/61 |
| 5,219,877 | | 6/1993 | Shah et al. | 514/399 |
| 5,264,206 | * | 11/1993 | Bohn et al. | 424/61 |
| 5,346,692 | | 9/1994 | Wohlrab et al. | 424/61 |
| 5,464,610 | | 11/1995 | Hayes, Jr. et al. | 424/61 |
| 5,487,776 | | 1/1996 | Nimni | 106/18.35 |
| 5,620,980 | * | 4/1997 | Samour | 514/256 |
| 5,696,105 | | 12/1997 | Hackler | 514/172 |
| 5,696,164 | * | 12/1997 | Sun et al. | 514/562 |
| 5,753,256 | | 5/1998 | Cordes et al. | 424/443 |
| 5,840,283 | | 11/1998 | Sorenson et al. | 424/61 |
| 5,993,787 | * | 11/1999 | Sun et al. | 424/59 |

OTHER PUBLICATIONS

K.A. Walter, et al., Permeability characteristics of the human nail plate, Int. Journal of Cosmetic Science, 5, 231–246 (1983).

Jean–Paul L. Marty, Amorolfine nail lacquer: a novel formulatin, Journal of European Acad. of Derm. and Venereology, 4(Suppl.1)S17–S21, (1995).

Mast, Nail Products, pp. 277–280.

Walters, Kenneth A., Penetration of chemicals into, and through, the nail, Pharm Int. Apr. 1985; p. 85–89.

Kligman, Albert M., Topical Pharmacology and Toxicology of Dimethyl Sulfoxide—Part I, Am. J. Med. Ass., 193, 1965, pp. 796–804.

* cited by examiner

*Primary Examiner*—Thurman K. Page
*Assistant Examiner*—Si Howard
(74) *Attorney, Agent, or Firm*—Sherman & Shalloway

(57) ABSTRACT

A nail lacquer effective for the treatment or prevention of fungal infections, such as, onychomycosis, includes fungicidally effective amount of ciclopirox, econazole, or other antifungal agent in a clear, stable, film-forming lacquer vehicle which includes a water-insoluble film-forming polymer; 2-n-nonyl-1,3-dioxolane or similar penetration enhancer; and volatile solvent. A plasticizer for the film-forming polymer which is also compatible with the other components may be included although the preferred penetration enhancers may also function as plasticizer. The composition, when applied to the nails provides a hard, clear, water-resistant film containing the antifungal agent. The film is resistant to multiple washings and is effective in the treatment of onychomycosis.

40 Claims, 2 Drawing Sheets

Release of drug (μg/h)
200
175
150
125
100
75
50
25
0
0 4 8 12 16 20 24
Time (h)
5% Econazole Lacquer

ANTIFUNGAL NAIL LACQUER AND METHOD USING SAME

CROSS-REFERENCE TO RELATED APPLICATION

This application claims the benefit of provisional application Ser. No. 60/074,025, filed Feb. 9, 1998.

BACKGROUND OF THE INVENTION (1). Field of Invention

This invention relates to antifungal nail lacquer compositions and to the treatment of onychomycoses or other fungal infestations affecting toe nails or finger nails using the nail lacquer composition. More particularly, the invention relates to antifungal nail lacquers which when applied to nails form strongly adherent, water-resistant, clear films; and to the method for treating or preventing fungal infestations of animal nails by applying the antifungal composition to the infected nail or to the fungal susceptible nail.

(2). State of the Prior Art

Fungal infection of the nails, commonly referred to as onychomycosis, is most frequently caused by dermatophytes but also can be caused by molds and Candida. Mixed infections also occur. Onychomycosis includes dermatophyte infection of the nail plate and includes infection of nails by any fungus, including yeast or molds. Thus, for example, onychomycosis serves as a reservoir for dermatophytes and contributes to treatment failure and recurrence of tinea pedis.

Most common causes of tinea unguium are *Trichophyton rubrum* (most frequent), *T. mentagrophytes*, and *Epidermophyton floccusum*. Onychomycosis due to nondermatophytes is usually caused by Candida species.

Nail lacquers for the treatment of onychomycoses and similar fungal infections affecting nails (toe nails and/or finger nails) of humans, in particular, or other animals, are known. Representative examples are described in the patent literature, of which the following U.S. Pat. Nos. can be mentioned: 4,957,730 (1-hydroxy-2-pyridone in water-insoluble film-former); 5,120,530 (amorolfine in quaternary ammonium acrylic copolymer); 5,264,206 (tioconazole, econazole, oxiconazole, miconazole, tolnaftate, naftifine hydrochloride, in water-insoluble film-former); 5,346,692 (with urea and dibutyl phthalate plasticizer); 5,487,776 (griseofulvin as colloidal suspension).

Other U.S. Pat. Nos. which relate to antifungal products include, for example, 4,636,520 (combination of imidazole and pyrrolnitrin); 5,002,938 (gel, combination of imidazole and 17-ester corticosteroid antiinflammatory agent); 5,110,809 (antifungal gel plus steroid); 5,219,877 (gel product with imidazole antifungal optionally with steroidal antiinflammatory, in a vehicle system that includes lauryl alcohol); 5,391,367 (aqueous alcoholic gel with tioconazole); 5,464,610 (salicylic acid plaster); 5,696,105 (mometasone furoate).

Effectiveness of nail lacquers as a delivery vehicle for topically administering the antifungal agent amorolfine is described by Jean-Paul L. Marty, J. of the European Academy of Dermatology and Venereology, 4(Suppl. 1), pp.S17–S21 (1995). As described by the author, the film-generating solution as the lacquer base for the active principle basically consists of volatile solvent (ethanol, ethyl/butyl/methyl acetate, methylene chloride, methyl ethyl ketone, isopropanol), and a non-water-soluble polymer (methacrylic acid copolymers, vinyl polymers) which leaves a thin continuous film following evaporation of the solvent. Plasticizers (triacetin, dibutyl phthalate) impart sufficient mechanical flexibility to prevent flaking and removal. Marty further notes the similarity of the film-generating solution to the nail lacquers used in cosmetics.

It is further explained that the specific aims addressed in formulating the film-generating solution of the anti-fungal nail lacquer include obtaining maximal affinity of the active principle to the nail keratin and obtaining the highest possible thermodynamic activity compatible with maintaining the active principle in true or supersaturated solution.

Differences in diffusion characteristics between nail and skin are also discussed in the Marty article. The nail structure is characterized as a water-gel in which water facilitates diffusion of at least polar compounds. In contrast, the skin tends to more readily facilitate diffusion of lipophilic, non-polar molecules, through the extracellular lipids of the stratum corneum. Thus, since the absolute transmission of water vapor through nails is about 10 times that through skin, and since nails are approximately 100 times as thick as stratum corneum, the permeability of nails to water vapor is about 1000 times greater.

Therefore, Marty reports that "excipients developed for use on skin are thus inappropriate for releasing active principles on the nail, as shown by the inefficacy of diffusion promoters such as DMSO" (citing Walters K A, Penetration of chemicals into, and through, the nail plate. Pharm Int. 1985; April, p. 85–89).

It has also been suggested in the literature (Mast, "Nail Products". . . ) that "[a]s a working hypothesis, it should be assumed that nails are, in general, quite permeable to polar and semipolar low molecular weight chemicals." See also, Walters K A and Flynn G L, "Permeability characteristics of the human nail plate" Intl J. of Cosmetic Science, 5, 231–246 (1983) for a review of the structure and characteristics of the nail and a discussion of permeation through the nail plate of various chemicals and permeation coefficients of $C_1$–$C_{12}$-alcohols.

These authors conclude, on the basis of the accumulated data that in connection with the successful formulation of drugs used in the treatment of nail infections, "that solvents with proven efficacy as skin 'penetration enhancers' show little promise as enhancers of nail plate permeability" (citing to Walters, K A and Flynn G L, J. Pharm. Pharmac. 33 6P (1981) and Kligman, A M J. Amm. Med. Ass. 193 796–804 (1965).

Nevertheless, there remains a need for more effective and more durable (longer lasting) nail lacquer formulations which incorporate an antifungal agent.

There also remains a need for an antifungal nail lacquer formulation which provides clear and glossy films which are capable of resisting multiple washings.

It is also known in the art, as indicated by several of the patent documents discussed above, that the overall effectiveness of antimycotic products for treating fungal infections of the skin may often be improved by combining the antifungal agent with a steroidal antiinflammatory agent. To date however such combination products have not been formulated into a lacquer type product for the treatment of onychomycosis but, rather, have been limited to gels, lotions, creams and other topically applied solutions.

SUMMARY OF INVENTION

Figure 1:
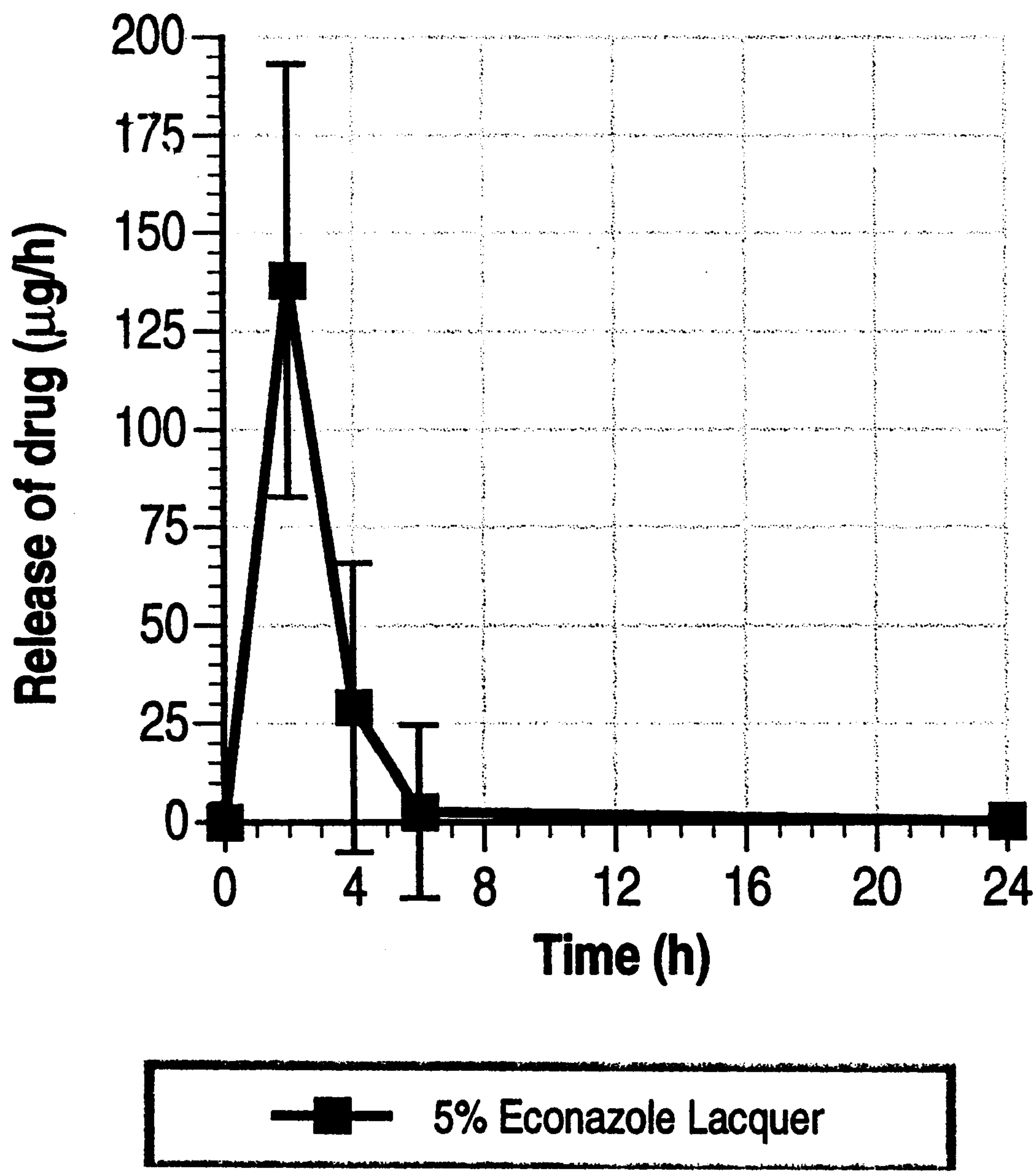
FIG. 1 is a graphical presentation of release rate (μg/h) of econazole as a function of time from the invention lacquer of Example 2.

The present invention aims to solving the above needs. Thus, according to the present invention there is provided a stable, nail lacquer formulation incorporating an antifungal agent, which formulation, when applied to nails yields a hard, durable, substantially clear, long lasting film, effective in the treatment or prevention of fungal infestations or infections on or associated with nails.

In particular, the present invention provides a composition effective for the treatment or prevention of fungal infections of nails, comprising:

(a) at least one antifungal agent effective in the treatment or prevention of onychomycoses;

(b) penetration enhancing agent selected from the group consisting of $C_7$–$C_4$-hydrocarbyl substituted 1,3-dioxolane, $C_7$-$C_{14}$-hydrocarbyl substituted 1,3-dioxane and $C_7$-$C_{14}$-substituted acetal;

(c) water-insoluble, film-forming polymer; and, (d) volatile solvent, the composition, when applied to nails, forming, upon evaporation of the volatile solvent, a hard, water-resistant film from which the antifungal agent is releasable and becomes available to treat or prevent fungal infection.

In a particular embodiment of the invention a nail lacquer composition is provided which includes a combination of an antifungal or antimycotic agent and a steroidal antiinflammatory agent in a solution of film-forming polymer in at least one volatile solvent; the composition may also include at least one penetration enhancing agent selected from the group consisting of $C_7$–$C_{14}$-hydrocarbyl substituted 1,3-dioxolane, $C_7$–$C_{14}$-hydrocarbyl substituted 1,3-dioxane and $C_7$–$C_{14}$-substituted acetal. A plasticizer for the film-forming polymer may also be included.

The invention also provides lacquer compositions effective for providing long-lasting, water-resistant adherent films on animal (e.g., human) skin and nails comprising a substantially non-aqueous solution of water-resistant, film-forming polymer, and plasticizing effective amount of at least one compound selected from the group consisting of $C_7$–$C_{14}$-hydrocarbyl substituted 1,3-dioxolane, $C_7$–$C_{14}$-hydrocarbyl substituted 1,3-dioxane and $C_7$–$C_{14}$-substituted acetal in volatile solvent.

The resulting water-resistant, adherent films provide novel products especially suitable as a delivery matrix for drugs, including the antifungal agents and others. When such film with drug incorporated therein, is deposited on animal, especially human or other mammal, skin or nail, the drug will leach from the film and will be capable of being absorbed by or transported into and through the skin or nail.

DETAILED DESCRIPTION AND PREFERRED EMBODIMENTS

The present invention provides still further improvements in the physical properties (e.g., durability, water-resistance, flexibility) of water-insoluble adherent films provided upon evaporation of the volatile solvent from the film-generating solution of nail lacquer composition, as well as improved diffusion characteristics of active principle(s) included in the lacquer composition from the resulting film.

The present invention makes it possible to effectively incorporate two, generally chemically dissimilar active principles: an antifungal agent and a steroidal antiinflammatory agent in a nail lacquer effective in treatment of onychomycosis.

The improvement in nail lacquer products according to the present invention is, in part, made possible by the incorporation into the film-generating solution of a specific class of penetration enhancing agent, namely, $C_7$–$C_{14}$-hydrocarbyl substituted 1,3-dioxolanes, 1,3-dioxanes and acetals, which have previously been described as enhancers for penetration of various pharmacologically active principles through the skin, and commercially available from MacroChem Corporation, Lexington, Mass., under the SEPA® trademark. The SEPA® skin penetration enhancers (hereinafter may be referred to as SPE's) are the subject matter of several issued U.S. Pat. Nos., including, 4,861,764, 5,391,567, 4,910,020, and 5,620,980, issued to one or more of the current inventors, and the disclosures of which are incorporated herein by reference thereto.

The preferred SPE's for use in the present invention may be represented by the following general formulas:

2-substituted 1,3-dioxolanes of the formula (I):

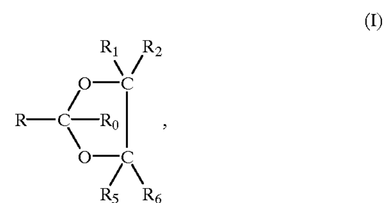

2-substituted 1,3-dioxanes of the formula (II):

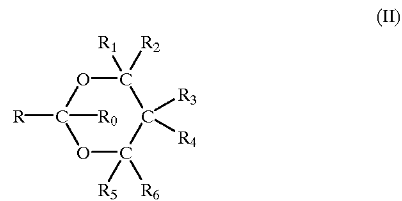

substituted-acetals of the formula (III):

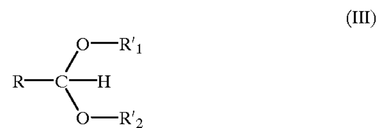

In the above formulas (I), (II) and (III) R preferably represents a $C_7$ to $C_{14}$ hydrocarbyl group, $R_0$, $R_1$, $R_2$, $R_3$, $R_4$, $R_5$, and $R_6$, each, independently, represent hydrogen or a $C_1$ to $C_4$ alkyl group.

$R'_1$ and $R'_2$, each, independently, represent $C_1$ to $C_4$ alkyl group.

The hydrocarbyl group for R may be a straight or branched chain alkyl, alkenyl or alkynyl group, especially alkyl or alkenyl. Preferably, R represents a $C_7$ to $C_{12}$ aliphatic group; especially $C_7$ to $C_{10}$ aliphatic group. Examples of suitable alkyl groups include, for example, n-heptyl, n-octyl, n-nonyl, n-decyl, n-undecyl, n-dodecyl, 2-methyl-octyl, 4-ethyl-decyl, 8-methyl-decyl, and the like. The straight chain alkyl groups, such as n-heptyl, n-octyl, n-nonyl and n-decyl, are especially preferred. Examples of alkenyl groups include, for example, 2-hexenyl, 2-heptenyl, 2-octenyl, 2-nonenyl, 2',6'-dimethyl-2',6'-heptadienyl, 2',6'-dimethyl-2', heptenyl, and the like. The R group may also be substituted by, for example, halo, hydroxy, carboxy, carboxamide and carboalkoxy.

The $C_1$ to $C_4$ alkyl group may be, for example, methyl, ethyl, n-propyl, isopropyl, n-butyl, tert-butyl, and the like. The preferred alkyl groups for $R_0$, and for $R_1$ to $R_6$ and for $R'_1$ and $R'_2$ are alkyl having 1 or 2 carbon atoms, most especially ethyl. $R_0$, and $R_1$ to $R_6$ may also, preferably, all be hydrogen.

Specific enhancer compounds include, for example, 2-n-heptyl-1, 3-dioxolane, 2-n-nonyl-1,3-dioxolane, 2-n-undecyl-1,3-dioxolane, 2-n-nonyl-1,3-dioxane, 2-n-undecyl-1,3-dioxane, 2-n-heptylaldehyde-acetal, 2-n-octyl-aldehyde-acetals, e.g., 2-n-octyl-aldehyde-dimethylacetal; 2-n-nonylaldehyde-acetals, 2-n-decylaldehyde-acetals, 3,7-dimethyl-2,6-octadienal (citral) acetals, citronal acetals and the like. 2-n-nonyl-1,3-dioxolane (2-NND), and decanal dimethyl or diethyl acetals are especially preferred. Mixtures of these compounds may also be used.

The amount of enhancer compound is selected to provide the desired delivery rate for the active compound but, taking into consideration such additional factors as, product stability, side effects, carrier system and the like. Generally, depending on the particular antifungal agent and film-forming polymer, amounts of the enhancer compound in the range of from about 0.5 to 35%, preferably from about 2 or 3 up to about 25 or 30 percent, especially from about 5 to 20 or 25 percent, by weight of the total composition, will provide optimal transungal delivery of the active principle over the duration of the film on the nail. From a practical matter, using the preferred enhancer compounds and film-forming polymers, optimum results (release and skin permeation characteristics) may usually be achieved without incorporating additional co-solvents or plasticizers, using amount of enhancer in the range of from about 12% to about 24% by weight, especially, from about 15% to about 20% by weight, based on the total weight of the composition, of the enhancer compound.

In this regard, it has been found that the SEPA® SPE's are not only effective to facilitate diffusion of the active agent(s) transungually but, quite surprisingly, in addition, the SEPA® family of compounds, function as adhesion promoters and, as plasticizers, for the film-forming polymer of the subject nail lacquer compositions, especially for compatible acrylate and methacrylate copolymers and copolymers of maleate esters with vinyl ethers. Compatibility between the film-forming polymer and the SEPA enhancer compounds may be readily determined by one of ordinary skill in the art, such as, for example, by formation of a single homogenous phase when the polymer and enhancer are mixed together. As will be appreciated by those skilled in the art, various factors, such as, for example, polarity of "mer" units of the polymer, molecular weight, and the like, will be considered for compatibility.

Although the reason for the enhanced transungual diffusion has not yet been fully elucidated, it is hypothesized that the SEPA® compounds function as plasticizing agents for the film-forming polymer and as solubilizing agent for the antifungal agent and other active principles, if any, upon evaporation of the volatile solvent, thereby making it easier for the active agent(s) to diffuse through and be released from the dry lacquer film. At the interface between the lacquer film and the nail the combination of SPE and active agent becomes available to penetrate into and through the nail.

The plasticizing and adhesion promoting functions, of the subject hydrocarbyl substituted 1,3-dioxolanes, 1,3-dioxanes and acetals are not, of course, restricted to the resulting films incorporating antifungal agent used as antifungal nail lacquers, but also are more generally exhibited with the below-described film-forming polymers, for virtually any drug which may be dissolved in the polymer/enhancer compound matrix, with or without the assistance of solvents or co-solvents. Thus, drugs which may be topically administered to the skin as well as drugs which are adapted for use in treating nails for onychomycoses or other ailments, may be incorporated into the nail and skin-adherent polymer plus enhancer compound film-forming composition of this invention.

The film-forming polymers which may be used in the present invention are not particularly limited and may be chosen from among any of the film-forming polymers previously used in or useful for nail lacquer film-forming polymers and which are compatible with the SPE and which have good adhesion to nail keratin (and/or skin) and form water-insoluble and/or water-resistant films which permit release of the antifungal agent and also the steroidal antiinflammatory agent, if present.

Examples of water-insoluble, film-forming polymers which may be used in the nail lacquer compositions of this invention, include, for example, polyvinyl acetate, mixed polymers (or copolymers) of vinyl acetate with acrylic or methacrylic acid, copolymers of (meth)acrylic acid and (meth)acrylate esters, copolymers of (meth)acrylic acid esters with amino group and/or quaternary ammonium group- containing comonomers, and the like. These polymers may be used alone or in mixtures with each other or with other film-forming polymers that will not impair the objectives of this invention.

As used in this application, the term "lower" in connection with "alkyl", etc., refers generally to carbon chain lengths of up to 6 carbon atoms, however, the preferred lower alkyl groups typically have from 1 to 4 carbon atoms.

Especially preferred film-forming polymers include acrylate (co)polymers, methacrylate (co)polymers, and copolymers of alkyl vinyl ether and maleic anhydride. For example, a preferred acrylic copolymer comprises recurring units of at least one of the following moieties (IV) and (V):

(IV)

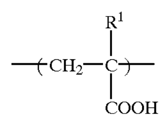

(V)

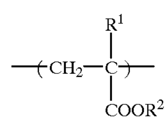

wherein $R^1$ represents H or $CH_3$; and $R^2$ represents an alkyl group of from 1 to about 12 carbon atoms, preferably from about 2 to about 12 carbon atoms, especially preferably, from about 4 to about 10 carbon atoms. The alkyl group may be linear or branched. Examples of alkyl groups for $R^2$ include methyl, ethyl, propyl, isopropyl, t-butyl, isobutyl, n-butyl, n-pentyl, 4-methyl-n-pentyl, n-hexyl, n-heptyl, n-octyl, 2-methyloctyl, n-nonyl, n-decyl, n-dodecyl, and the like.

Another useful acrylic copolymer comprises recurring units of a moiety of formula (VI)

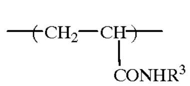

wherein $R^3$ represents an alkyl group, such as, for example, the alkyl groups described above for $R^2$; preferably an alkyl group of at least two and up to about 12 carbon atoms, especially preferably $C_4$ to $C_{10}$ alkyl.

Acrylic copolymers which comprise recurring units of formula (V) or formula (VI) or both formulas (V) and (VI), and, optionally, recurring units of formula (IV), as defined above, wherein at least one of $R^2$ and $R^3$ represents an alkyl group having at least 4 carbon atoms, are particularly preferred.

Another preferred class of acrylic copolymer comprises recurring units of acrylic and/or methacrylic acid esters and recurring units of a moiety containing a cationic amine and/or quaternary ammonium group, such as, for example, carboethoxy-t-butyl ammonium. As is well known in the art, the cationic amine group may be quaternized by reaction of the amine with an alkylating agent or other appropriate reagent to form a salt.

For example, any of the water-insoluble quaternary ammonium group containing acrylic copolymers disclosed in the aforementioned U.S. Pat. No. 5,120,530, the disclosure of which is incorporated herein by reference thereto, may be used as the film-forming copolymer in the compositions of the present invention.

Another preferred example of the water-insoluble, film-forming polymer comprises a copolymer of alkyl vinyl ether, such as, for example, methyl vinyl ether or ethyl vinyl ether, and at least one comonomer of a monoester of a dicarboxylic acid. Examples of such comonomer of a monoester of a dicarboxylic acid are shown by the following formula (VII):

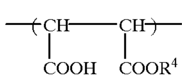

wherein $R^4$ represents a lower alkyl group, especially an alkyl group of from 1 to 4 carbon atoms, such as, for example, methyl, ethyl, propyl.

See also the film-forming polymers disclosed in the aforementioned U.S. Pat. Nos., 5,264,206, and the other patents mentioned above, which may also be used in this invention.

Film-forming polymers useful in the present invention are commercially available, such as, for example, the acrylic copolymers sold by National Starch Co. under the tradename Dermacryl, e.g., Dermacryl 79, Dermacryl LT; the amine or quaternary ammonium group containing acrylic copolymers sold by Rohm (a division of Huls Group) under the tradename Eudragit, e.g., Eudragits E, RS, RL,; the methylvinyl ether copolymers sold by ISP Corp. under the tradename Gantrez, e.g., Gantrez ES-335I, Gantrez ES-425, ES-435; the quaternary ammonium acrylic copolymers sold by National Starch Co. under the tradename Amphomer, e.g., Amphomer LV-71. Particularly good results have been obtained with each of the following commercially available products:

Gantrez ES-425:

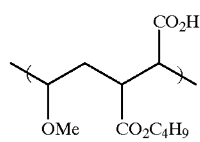

Eudragit RL:

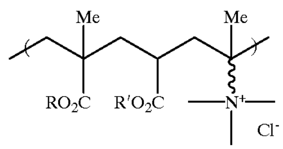

Cationic

Dermacryl 79 &
Dermacryl LT:

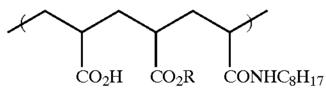

Anionic

Amphomer LV-71:

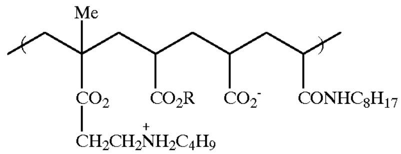

Amphoteric

The amount of film-forming polymer will depend on such factors as, for example, the molecular weight of the polymer, the desired thickness of the resulting film, the degree of water-resistance and the intended duration and delivery rate of the active agent(s), the compatibility with the other ingredients, and the like. Usually, however, satisfactory results are obtained when the amount of film-forming polymer is in the range of from about 10 to about 70 percent, preferably from about 15 to about 50 percent, especially from about 20 to 40 percent by weight of the total nail lacquer composition.

In terms of weight ratio between film-forming polymer and penetration enhancing (and plasticizing) dioxolane, dioxane or acetal compound, suitable values of polymer:enhancer/plasticizer generally range from about 4:1 to about 1:1, preferably from about 3:1 to about 1.2:1, especially preferably from about 2:1 to about 1.2:1. The plasticizing function of the enhancer compounds is exhibited over generally the same or somewhat higher concentrations as the skin penetration enhancing function. Therefore, when other plasticizing additives, as described below, are included in the compositions of this invention, the ratio of polymer to enhancer may be somewhat higher than the above ranges, for example, from about 5:1 to about 1:1.

Conventional plasticizers compatible (e.g., forming a homogenous film) with film-forming polymers may be included in the compositions of this invention to provide additional flexibility to the dried polymer film upon evaporation of the solvent, and/or additional releasability of the antifungal agent (and antiinflammatory, when present) as well as for the SPE compound. Suitable plasticizers include, for example, 1,2,3-propanetriol triacetate (triacetin), dibutyl phthalate, dioctyl phthalate, dibutoxy ethyl phthalate, diamyl phthalate, sucrose acetate isobutyrate, butyl acetyl ricinoleate, butyl stearate, triethyl citrate, dibutyl tartrate, polyethylene glycol, dipropylene glycol, polypropylene glycols, propylene glycol, glycol fatty acid esters, such as, propylene glycol dipelargonate, and the like.

Particularly preferred plasticizers are glycols, such as propylene glycol and dipropylene glycol, glycol esters, phthalate esters, citrate esters, polyethylene glycols, and polypropylene glycols.

The type and amount of plasticizer, when present in the formulation, affects resistance of the dried polymer film to water and also affects the release rate of the active drug ingredients as well as that of the SPE. Those skilled in the art will recognize that the degree of water resistance can also be controlled by the type and amount of the plasticizer(s), the nature of the active principles, the choice of polymer (e.g., amount of acid groups in the polymer, etc.), the amount of the polymer, and the like.

When the additional plasticizer is present it will generally be used in amounts which depend on the types and amounts of the film-forming polymer and the SPE, most usually in the range of from about 0.5 to about 20 percent, preferably from about 2 to 10 percent, especially, from about 4 to 8 percent, based on the total weight of the composition.

While additional plasticizers may be incorporated in the invention compositions, as noted above, in view of the surprising plasticizing effect of the subject skin penetration enhancing compounds, sufficient flexibility and adhesion, as well as compatibility (both wet and dry) between the respective ingredients, is usually achieved without the addition of conventional plasticizers.

Solvents which may be used in the nail lacquer compositions of this invention are also not particularly critical but may be selected from among the usual physiologically safe organic solvents for lacquer compositions, so long as the active principles and film-forming polymers are soluble therein and so long as the lacquer is easy to apply and sufficiently volatile to provide acceptable drying times, usually dry to the touch in less than about 5 minutes, preferably less than about 2 minutes. As examples of such solvents mention may be made of lower alkanols, e.g., ethanol, propanol, isopropanol, butanol, isobutanol; lower alkyl esters of lower carboxylic acids, e.g., ethyl acetate, propyl acetate, n-butyl acetate, n-amyl acetate; lower alkyl ethers, e.g., methyl ether, methyl ethyl ether; lower alkyl ketones, e.g., methyl ethyl ketone; halogenated hydrocarbons, e.g., methylene chloride, methyl chloroform; aromatic hydrocarbons, e.g., toluene; cyclic ethers, such as, tetrahydrofuran, 1,4-dioxane; and mixtures thereof. Anhydrous ethanol (EtOH) is especially preferred.

The solvents used in the nail lacquer formulations of this invention are generally and preferably non-aqueous. However, in some cases small amounts of water, generally less than about 10%, preferably less than about 5% by weight of total solvents, may be used if not substantially impairing the homogeneity, clarity and solubility of the various ingredients in the lacquer solution. For example, ethanol when used may sometimes be added in the form of a 95% ethanol solution.

Again, in view of the good compatibility between the film-forming polymer and the dioxolane, dioxane and acetal enhancer/plasticizer compounds, use of co-solvents, such as propylene glycol, in addition to solvent, e.g., ethanol, are usually not required and, therefore, may be omitted.

On the other hand, however, it may be desirable and, in some cases, preferred, to decrease the water-resistance of the dried polymer film, for example, to facilitate removal of the film after release of all or most of the active ingredients. Thus, it is envisioned that in addition to a lacquer film from which the active ingredients are released over periods of several days to about 1 week or longer, lacquer films from which the active ingredient is released over shorter periods of time, such as one day, may be desirable since many individuals are accustomed to and prefer treatments requiring applications of a drug on a daily basis.

Techniques for increasing the availability of the active ingredients for transungual delivery have been described above. When the active ingredient is exhausted from the film or mostly exhausted the film may be removed by application of suitable solvents, such as those described above, such as alcohols, acetone, ketones, etc., and/or by scraping or brushing, as also well known in the nail lacquer art.

Often, mixtures of volatile solvents of different boiling points, usually a low boiling solvent in the range of from about 40° C. to about 100° C. with a medium boiling solvent (boiling point up to about 150° C.) may be selected to provide drying times of no more than a few minutes or less, with uniform evaporation rates, good flow and viscosity characteristics and other desirable lacquer parameters, as well known in the cosmetic art. In some cases, high boiling point solvents, such as, for example, cellosolve, butylcellosolve acetate, butyl cellosolve, ethyl cellosolve, and the like, may be added in small amounts provided they do not impede the fast drying property and other desired characteristics.

In this connection, one of the important features of the compositions of the present invention is that all of the volatile and non-volatile ingredients are compatible with each other and form upon mixing clear solutions which are stable against phase separation over a wide temperature range above and below room temperature, such as, for example, from temperatures within the range of from about−10° C. to about+135° C.

Another important characteristic of the invention compositions is that the films formed upon evaporation of the solvent(s) and any other volatile components are strongly adherent to the nail and are water-resistant, namely, capable of withstanding repeated normal washing with soapy water for at least 1 day, usually up to about 5 or more days, preferably, at least one week, depending on the amount of antifungal agent with or without antiinflammatory agent in the film and upon the release rate of the active principles from the film. That is, it is possible to formulate the lacquer composition to remain strongly adherent and water-resistant for sufficiently long so as to last between applications and provide a therapeutically effective amount of the active ingredient(s) present in the dried lacquer film.

In addition, the dry films, for cosmetic appearance, should be substantially clear and transparent.

However, it is also within the scope of the invention to include colorants, such as pigments and/or dyestuffs, nacreous agents, pearlescent agents, fillers, and the like, to cover the nail, for example, to hide any unsightly manifestations of the fungal, yeast or other infection, or otherwise as may be cosmetically desirable.

Other conventional additives customarily present in cosmetic or medicinal nail lacquers may be included in the present formulations in their usual amounts so long as they do not interfere with the diffusion of the active principles and other parameters of the lacquer composition and dried polymer-film. Examples of such additives include, sedimentation retarders, chelating agents, antioxidants, silicates, aroma substances, wetting agents, lanolin derivatives, light stabilizers, antibacterial substances, and the like.

The lacquer compositions of this invention, with or without antifungal agent may be prepared following any of the procedures normally employed in the nail lacquer field, noting that most of the major, inactive ingredients are added as mobile liquids such that normal mixing techniques are available, with no particular order of addition of the respective ingredients being required. Generally, however, the polymer film-former, if in powder form, should be added gradually to some or all of the liquid components in such manner as to avoid clumping and resulting protracted dissolution times. Other ingredients may be added as convenient, as will be readily apparent to the practitioner.

The antifungal agent films obtained from the nail lacquers of this invention are effective in treating onychomycoses and other fungal infections. Usually, repeated applications of the antifungal lacquer will be made over a period of several weeks to several months, depending on the severity of the infection, the amount of active agent, and the condition of the nails of the patient. Since the antifungal agent containing film will contain sufficient active principle to be diffused through the nail over a period of at least 1 day, and up to about 7 days and, since the film will remain in place usually for the entire period of diffusion, applications of the antifungal nail lacquer need be repeated only about once per day to about once per week. For example, it may be desired to provide formulations for daily application during the initial period of usage until the patient observes substantial reduction in the degree and extent of infection and thereafter to provide different formulations designed for less frequent applications, such as every other day, weekly, etc.

In addition to treating an existing infection or fungal infestation, the nail lacquers of this invention may also be applied prophylactically to the nails of a healthy individual who is or who believes he or she may be at risk for a mycotic infection, as a result, for example, of occupation, geographical location or otherwise. The manner of use is otherwise identical to the use in treating an existing infection, however, smaller dosages, but still at least above the MIC of the antifungal agent, may be sufficient in many cases to prevent the onset of fungal infection in the event of fungal contamination or infestation.

There is no particular limitation on the antifungal agents used in the compositions of this invention; any of the agents known to be effective for this purpose may be used and a listing of such compounds may be found, for example, in any current edition of The Merck Index under the headings “Antifungal (Antibiotic)” and “Antifungal (Synthetic)” in the Therapeutic Category and Biological Activity Index section.

As examples of suitable antifungal agents mention may be made of, for example, polyenes, e.g., Natamycin, Nystatin; allylamines, e.g., Naftifine, Terbinafine; imidazoles, e.g., Bifonazole, Chlotrimazole, Econazole, Fenticonazole, Ketocanazole, Miconazole, Oxiconazole; triazoles, e.g., Fluconazole, Itraconazole, Terconazole; tolnaftate, ciclopirox, undecylenic acid, sulbentine, and morpholines, e.g., amorolfine, and the related morpholines disclosed in the aforementioned U.S. Pat. No. 5,120,530. The 1-hydroxy-2-pyridone compounds disclosed in U.S. Pat. No. 4,957,730, the disclosure of which is incorporated herein, by reference thereto, may also be used, as may the antifungal agents disclosed in any of the other patent documents discussed in the Background of the Invention.

In the present invention, the antifungal agents are, preferably, present in the free form, e.g., as acid or base, rather than in the form of their salts. In this regard, the free form of antifungal agent will usually have a higher diffusion rate through the nail than a salt of the same agent; or, the salt form of a drug may impair the water-resistance of the lacquer film.

The amount of the active antifungal agent or mixture of such agents in the composition will depend on such factors as its structure and antimicrobial activity, release rate from the polymer film, diffusion characteristics and penetration behavior in the nail. Generally, any amount effective to kill the infecting microorganism, which will generally be several to several tens to hundreds of times greater than the Mean Inhibitory Concentration (MIC), may be included in the nail lacquer (as applied) composition. Typically, amounts of active antifungal agent in the range of from about 0.5 to 20 percent by weight, preferably from about 1 to 10 percent, by weight, of the total composition (including solvents, film-forming polymer, enhancer, etc.) will suffice for compositions for treatment as well as compositions for prevention. The amount of antifungal agent in the dried film will, therefore, depend on the amount of agent in the lacquer solution and by the thickness of the applied film. The thickness of the film can be controlled by, for example, controlling the viscosity of the lacquer solution, such as by the type and amount of polymer, types and amounts of solvents, etc.

Conversely, on the basis of the non-volatile components of the composition, the amount of active agent is generally about 1 to 50%, preferably about 2 to 35%, more preferably, from about 2 to 30%, especially preferably from about 5 to 20%, by weight of the composition (film-forming polymer (s), active(s), plasticizer(s) and other non-volatile additives).

The antifungal nail lacquers according to this invention, by virtue of the incorporation of the penetration enhancer/plasticizer, as described above, provide therapeutically effective concentrations of antifungal agent deep into the nail bed. Although a precise minimum value of the therapeutically effective amount of antifungal agent will depend on several factors, primarily the particular antifungal agent and the degree and severity and cause of onychomycoses or other fungal infection, generally concentrations of antifungal agent greater than at least about 150 ppm in deep nail bed should be reached to attain favorable clinical results.

The compositions of this invention may also include a steroidal antiinflammatory agent in addition to the antifungal agent. While combinations of antifungal agent and steroidal antiinflammatory agent have been known in the past, there have been no known uses of such combinations in a nail lacquer compositions.

The steroidal antiinflammatory agent may be selected from among any of the known steroidal antiinflammatory agents, including, for example, any of those disclosed in The Merck Index or in any of the aforementioned U.S. Pat. Nos. 5,002,938, 5,110,809, 5,219,877, the disclosures of which are incorporated herein by reference thereto. As examples of steroidal antiinflammatory agents useful in the compositions of the present invention mention may be made of, for example, 21-acetoxypregnenolone, alclometasone or its dipropionate salt, algestone, amcinonide, beclomethasone or its dipropionate salt, betamethasone and salts thereof, including, for example, betamethasone benzoate, betamethasone dipropionate, betamethasone sodium phosphate, betamethasone sodium phosphate and acetate, and betamethasone valerate; clobetasol or its propionate salt, clocortolone pivalate, hydrocortisone and salts thereof, including, for example, hydrocortisone acetate, hydrocortisone butyrate, hydrocortisone cypionate, hydrocortisone phosphate, hydrocortisone sodium phosphate, hydrocortisone sodium succinate, hydrocortisone tebutate and hydrocortisone valerate; cortisone acetate, desonide, desoximetasone, dexamethasone and salts thereof, for example, acetate and sodium phosphate; diflorasone diacetate, fludrocortisone acetate, flunisolide, fluocinolone acetonide, fluocinonide, fluorometholone, flurandrenolide, halcinonide, medrysone, methylprednisolone and salts thereof, e.g., acetate, sodium succinate; mometasone furoate, paramethasone acetate, prednisolone and salts thereof, e.g., acetate, diethylaminoacetate, sodium phosphate, sodium succinate, tebutate, trimethylacetate; prednisone, triamcinolone and derivatives thereof, e.g., acetonide, benetonide, diacetate, hexacetonide. Other glucocorticoid steroids reported in the literature, including The Merck Index, or otherwise approved by the local drug regulatory agency, e.g., Food and Drug Administration, may also be used.

Particularly preferred steroidal antiinflammatory agents include clobetasol and its salts, e.g., propionate salt; betamethasone and its salts, hydrocortisone and its salts, and triamcinolone and its salts.

Although not particularly limited, the antiinflammatory agent will usually be present in the lacquer composition in an amount within the range of 0.01 to about 5 percent, preferably from about 0.1 to 2 percent, based on the total weight of the solution.

The total amount of antifungal agent and antiinflammatory agent will usually range from about 0.5 to about 30 percent, by weight, preferably from about 1 to 25 percent by weight, especially from about 1.5 to about 12 percent by weight, based on the total weight of the lacquer composition, i.e., the lacquer solution.

The following examples illustrate various compositions according to the invention but are not intended to and should not be construed to in any manner limit the scope of the invention.

EXAMPLE 1

The nail lacquer compositions shown in the following table were prepared. Each composition was observed for compatibility. The results of the observations are shown in the table. In addition, each nail lacquer composition was applied to a glass substrate and allowed to dry in air and the state (homogeneity) of the dried lacquer films were observed. The results are also reported in the following Table 1.

TABLE 1

| | Antifungal Lacquers | | | | | | | | | | | | | |
|---|---|---|---|---|---|---|---|---|---|---|---|---|---|---|
| MC No. | 1<br>16017A | 2<br>18229B | 3<br>16070A | 4<br>16071D | 5<br>16074A | 6<br>16074B | 7<br>16074C | 8<br>18234A | 9<br>18234B | 10<br>18234C | 11<br>18234D | 12<br>18240A | 13<br>18236E | 14<br>18242A |
| 1. Econazole | 2 | 2 | 5 | 5 | 5 | 5 | 5 | 5 | 5 | 5 | 5 | 5 | 5 | 5 |
| 2. Miconazole | — | — | — | — | — | — | — | — | — | — | — | — | — | — |
| 3. Ciclopirox | — | — | — | — | — | — | — | — | — | — | — | — | — | — |
| 4. Hydro-cortisone | — | — | — | — | — | — | — | — | — | — | — | 1 | — | — |
| 5. 2-Nonyl-1,3-dioxolane | 6 | 6 | 6 | 6 | 6 | 6 | 6 | 6 | 6 | 6 | 6 | 6 | 6 | 12 |
| 6. Citral ethylene glycol acetate | — | — | — | — | — | — | — | — | — | — | — | — | — | — |
| 7. Decanal dimethylacetal | — | — | — | — | — | — | — | — | — | — | — | — | — | — |
| 8. Propylene glycol | 20 | 20 | 20 | — | 6 | 6 | 6 | — | — | — | — | 6 | 6 | 6 |
| 9. Amphomer LV-7 | 24 | — | — | 24 | 24 | 24 | 24 | 24 | 24 | 24 | 24 | 24 | — | 24 |
| 10. Amphomer | — | — | — | — | — | — | — | — | — | — | — | — | 24 | — |
| 11. Dermacryl LT | — | — | 24 | — | — | — | — | — | — | — | — | — | — | — |
| 12. Dermacryl 79 | — | 24 | — | — | — | — | — | — | — | — | — | — | — | — |
| 13. Ethanol | 48 | 48 | 45 | 65 | — | 34 | 49 | 59 | 59 | 59 | 59 | 58 | 59 | 53 |
| 14. Acetone | — | — | — | — | 59 | — | — | — | — | — | — | — | — | — |
| 15. Ethyl acetate | — | — | — | — | — | 25 | 10 | — | — | — | — | — | — | — |
| 16. Diethyl ether | — | — | — | — | — | — | — | — | — | — | — | — | — | — |
| 17. Urea | — | — | — | — | — | — | — | 6 | — | — | — | — | — | — |
| 18. PEG 200 | — | — | — | — | — | — | — | — | 6 | — | — | — | — | — |
| 19. PPG 1K | — | — | — | — | — | — | — | — | — | 6 | — | — | — | — |
| 20. Di-propylene glycol | — | — | — | — | — | — | — | — | — | — | 6 | — | — | — |
| TOTAL | 100 | 100 | 100 | 100 | 100 | 100 | 100 | 100 | 100 | 100 | 100 | 100 | 100 | 100 |
| Com-patibilities*: | | | | | | | | | | | | | | |
| Wet[a] | C | C | C | C | C | C | C | C | C | C | C | C | C | C |
| Dry[b] | C | (a) | C | C | C | C | C | C | C | C | C | C | C | SH |

| | Antifungal Lacquers | | | | | | | | | | | | |
|---|---|---|---|---|---|---|---|---|---|---|---|---|---|
| MC No. | 15<br>18242B | 16<br>18242C | 17<br>18242D | 18<br>18245A | 19<br>18245B | 20<br>18245D | 21<br>18245F | 22<br>18236B | 23<br>18246A | 24<br>18246B | 25<br>18245C | 26<br>16908A | 27<br>17529B |

TABLE 1-continued

| | | | | | | | | | | | | | |
|---|---|---|---|---|---|---|---|---|---|---|---|---|---|
| 1. Econazole | 5 | 5 | 5 | 5 | 5 | 5 | 5 | 8 | 10 | 20 | — | — | — |
| 2. Miconazole | — | — | — | — | — | — | — | — | — | — | 5 | — | — |
| 3. Ciclopirox | — | — | — | — | — | — | — | — | — | — | — | 8 | — |
| 4. Hydrocortisone | — | — | — | — | — | — | — | — | — | — | — | — | — |
| 5. 2-Nonyl-1,3-dioxolane | 24 | 12 | 24 | — | — | — | — | 6 | 6 | 6 | 6 | 6 | 6 |
| 6. Citral ethylene glycol acetate | — | — | — | 6 | — | — | — | — | — | — | — | — | — |
| 7. Decanal dimethylacetal | — | — | — | — | 6 | — | — | — | — | — | — | — | — |
| 8. Propylene glycol | 6 | — | — | — | — | — | 6 | 6 | 6 | 6 | — | 6 | 6 |
| 9. Amphomer LV-71 | 24 | 24 | 24 | 24 | 24 | 24 | 24 | — | 24 | 24 | 24 | 24 | 24 |
| 10. Amphomer | — | — | — | — | — | — | — | 24 | — | — | — | — | — |
| 11. Dermacryl LT | — | — | — | — | — | — | — | — | — | — | — | — | — |
| 12. Dermacryl 79 | — | — | — | — | — | — | — | — | — | — | — | — | — |
| 13. Ethanol | 41 | 59 | 47 | 65 | 65 | 71 | 65 | 56 | 54 | 44 | 65 | 28 | 28 |
| 14. Acetone | — | — | — | — | — | — | — | — | — | — | — | — | — |
| 15. Ethyl acetate | — | — | — | — | — | — | — | — | — | — | — | 28 | — |
| 16. Diethyl ether | — | — | — | — | — | — | — | — | — | — | — | — | 28 |
| 17. Urea | — | — | — | — | — | — | — | — | — | — | — | — | — |
| 18. PEG 200 | — | — | — | — | — | — | — | — | — | — | — | — | — |
| 19. PPG 1K | — | — | — | — | — | — | — | — | — | — | — | — | — |
| 20. Dipropylene glycol | — | — | — | — | — | — | — | — | — | — | — | — | — |
| TOTAL | 100 | 100 | 100 | 100 | 100 | 100 | 100 | 100 | 100 | 100 | 100 | 100 | 100 |
| Compatibilities*: | | | | | | | | | | | | | |
| Wet[a] | C | C | C | C | C | C | C | C | C | C | C | C | C |
| Dry[b] | VH | C | SH | C | C | C | C | C | C | C | C | C | C |

| Ingredient | 28 | 29 | 30 | 31 | 32 | 33 | 34 |
|---|---|---|---|---|---|---|---|
| Econazole | 5 | 1 | 5 | 5 | 5 | 5 | 5 |
| 2-heptyl-1,3-dioxolane | | 6 | | 18 | | | |
| 2-nonyl-1,3-dioxolane | 6 | 6 | 5 | | | | 18 |
| Citral ethylene glycol acetal | | | | | 18 | | |
| Decanal dimethylacetal | | | | | | 18 | |
| Amphomer LV-71 | 24 | 24 | | | | | |
| Eudragit RL | | | 24 | 24 | 24 | 24 | 24 |
| Ethanol | 59 | 63 | 66 | 53 | 53 | 53 | 47 |
| PEG 200 | 6 | | | | | | |
| Triacetin | | | | | | | 6 |

*C = Clear/compatible; H = Hazy; S = Slightly; V = Very
[a]Complete lacquer,
[b]Air dried film
(a) crystallized
†2-(2',6'-Dimethyl-2',6'-heptadienyl)-1,3-dioxolane The compositions of Run Nos. 28–34 were also compatible and clear under wet and dry conditions.

Furthermore, in any of these examples, the lacquers with or without the antifungal agent will form flexible films which are strongly adherent to nails and other hard surfaces, including glass and metal substrates.

Moreover, these results (see, e.g., Run Nos. 23 and 24) show that the antifungal agent is very highly compatible in the invention films, such that crystallization, even at very high drug levels, is greatly inhibited. Thus, the 10% lacquer remained clear for more than a month after casting and drying and even a 20% (corresponding to 35% in the dry film) lacquer did not fully crystallize after drying.

Accordingly, the SEPA plasticization effect will increase bioavailability of drugs through decrease of diffusional barriers to release.

EXAMPLE 2

The following compositions were prepared and used in the tests described below:

| Ingredient | Wt. % |
|---|---|
| Econazole | 1–10 |
| 2-n-nonyl-1,3-dioxolane | 18 |
| Eudragit ® RL | 24 |
| Ethanol | q.s. 100 (57-48) |

Using the above formulation with 5% Econazole and 53% ethanol, stability testing was performed. There was no decomposition as indicated by lack of color changes of lacquers stored in clear or light protected containers under accelerated conditions. In addition, gas chromatography quantitative analysis was conducted on samples stored in glass containers for 50 days at 40° C./75%RH at varying pH (5.2, 6.83, 12.2; by addition of acid or base, as necessary).

The analytical test procedure involves a simple direct dilution and injection method for determining levels of both antifungal agent and enhancer compound in the same chromatogram, i.e., without separation steps. The test procedure detects a known primary degradant of econazole (i.e., 1-(2,4-dichloro-β-hydroxyphenethyl) imidazole) and a known primary degradant of the enhancer (i.e., the corresponding aldehyde, e.g., decanal for 2-n-nonyl-1,3-dioxolane). Specifically, a Hewlett-Packard Model 5890 Chromatograph with a Hewlett-Packard 50+(crosslinked 50% phenylmethylsiloxane), 30 m, 0.32 mm ID, 0.50μ film (Cat. #19091L) column and Model 7673 Autoinjector, operating in split mode (split flow 0.7 mL/min; split ratio 0.652:1), using methanol as wash solvent and hexanophenone as internal standard, was used for the analysis. The results are shown in the following Table 2. In Table 2 the results are reported for the average of six injections.

TABLE 2

| Run No. | pH | SEPA assay (%) | Econazole Assay (%) |
|---|---|---|---|
| 1 | 5.2 | 93.85 | 94.29 |
| 2 | 6.83 | 98.41 | 96.67 |
| 3 | 12.2 | 99.36 | 97.60 |

The following additional test procedures were used to evaluate the release and penetration characteristics of compositions according to the invention.

In Vitro Release Test for Lacauers

Using a 50 μl micropipette (VWR) set on 11 μl, approximately 10 mg of lacquer are applied homogeneously on frosted glass tile squares, 1 $cm^2$. This corresponds to the amount deposited on nails in the nail permeation method described below. Each tile is weighed out before and after applications of the lacquer and weights are recorded. The exact amount of lacquer applied is determined from the difference in the weight of the tile before and after treatment. Tiles are then placed on an orbital shaker set at 180 rpm at room temperature over the duration of the experiment.

Figure 2:
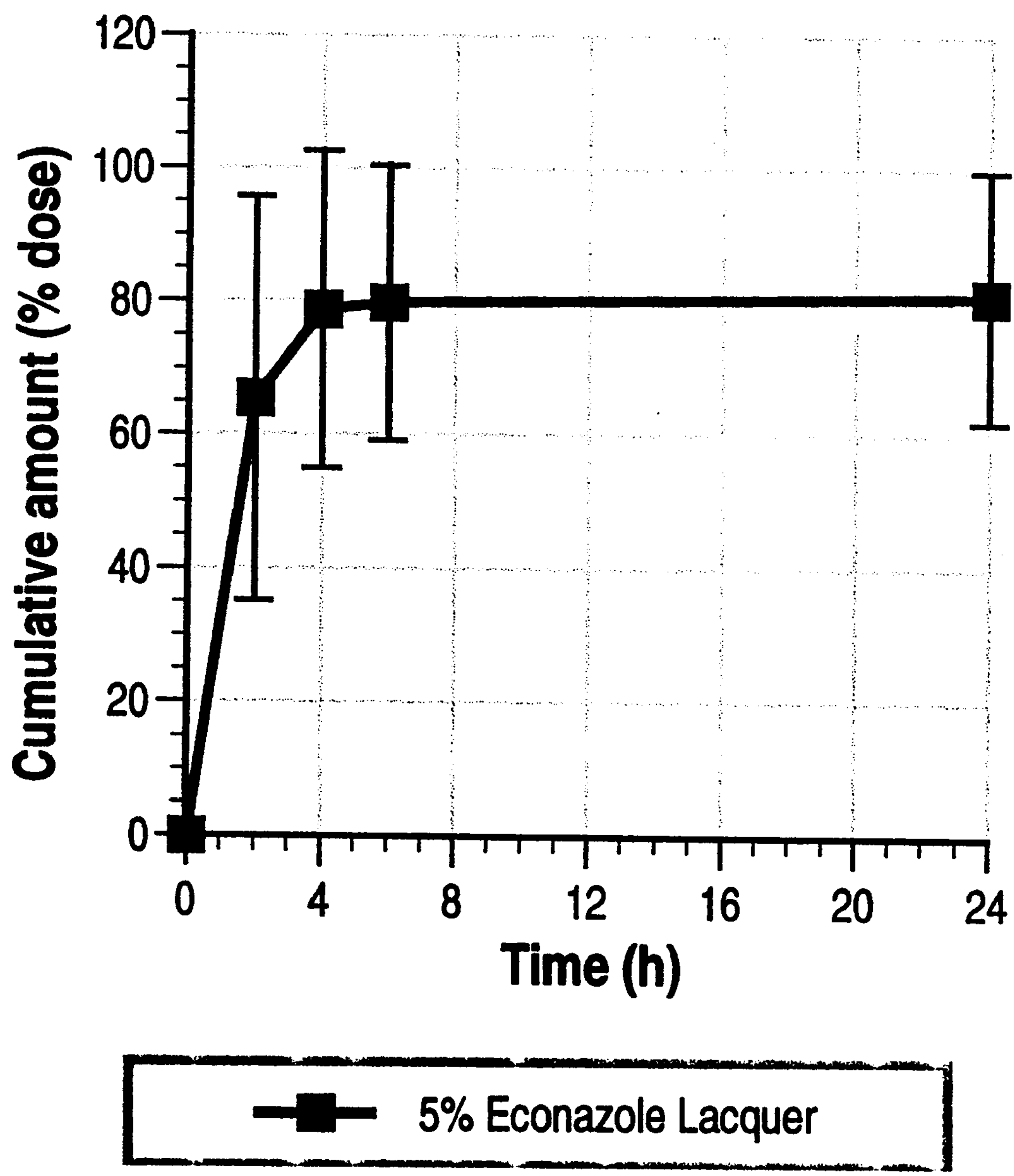
FIG. 2 is a graphical presentation of the release rate (% dose) of econazole as a function of time from the invention lacquer of Example 2.

Aliquots of 1 ml are collected from each vial 2, 4, 6, and 24 hours after the beginning of the agitation. Samples are poured into 2 ml HPLC vials and analyzed by the HPLC method for econazole (see below). Results are expressed as the amount of Econazole released in the milieu over time (μg/h) and as the cumulative amount of drug released expressed as percentage of drug and are shown in the accompanying FIGS. 1 and 2.

A satisfactory release profile shows 60% antifungal agent released to the milieu within 6 hours.

In Vitro Drug Delivery

HPLC Analysis of Econazole

The HPLC assay used is a reverse phase assay system using a Whatman RTF column: 40:55:5 (ACN:pH=3.01, 10 mM $KH_2PO_4$:$CH_3OH$); injection=24 μL (20 μL sample+ 4μL$H_3PO_4$), temperature=50° C., flow =0.9 mL/min; Samples in 80:20 ethanol:phosphate buffered saline (PBS). The assay is suitable for measuring econazole at low levels in analyte fluids. The HPLC software reports the final results in units of micrograms per ml of test solution.

EXAMPLE 3

Optimization Studies in Human Skin

Studies are performed in human organ transplant donor skin to optimize the release and subsequent skin permeation characteristics of lacquers of varying composition. These studies are designed to determine whether the characteristic advantageous drug delivery properties of the invention SPE's are retained when formulated into lacquers. The results demonstrate optimum release and permeation between 12 and 24% w/w SPE.

In Vitro Studies: Porcine Nail

Nail procedure: single application

Pig feet are obtained from an abattoir and are cleaned and washed with tap water. Nails are excised using scalpel and nail bed tissue is removed. Circlets are punched with a 1.2 cm diameter metallic punch. Each nail, depending on its size, provides an average of 3–4 circles. Nail circlets are packed in groups of 6 in gauze, soaked with phosphate buffered saline solution, and stored in a refrigerator at 2–8° C. until needed.

Petri dishes are prepared by filling with a gel, e.g., phosphate buffered saline:polyethylene glycol 200 (90:10) carbomer thickened gel (pH 5.13). The gel is spread evenly on the bottom of the petri dishes and is of sufficient consistency to support the nail circlets for the duration of the studies. Each dish could contain up to 6 nails.

Lacquer, approximately 10 mg, is applied evenly to each nail with an adjustable 50 μl micropipette (VWR) set to 11 μl. Each nail is weighed before and after application of the lacquer and weights are recorded. The exact amount of lacquer applied is determined from the difference in the weight of the nail before and after treatment. Nail circlets are then placed in groups of 6 on the gel and allowed to air dry for 10–15 minutes before covering the dishes. Dishes are subsequently placed in an incubator, set at 40–45° C., for the duration of the experiment.

At the end of the exposure time frame, the nails are removed, rinsed with deionized water, and placed individually into 20 ml vials. Ethanol (2 ml of 95%) is added and the vials are agitated for 15 minutes using an orbital shaker at 150–200 rpm. Supernatants are then collected into 4 ml vials. This washing is repeated with 2 ml of fresh ethanol and the supernatants combined. A 100 μl aliquot is added to an HPLC vial containing 900 μl PBS to a final 1/10 dilution and analysed by HPLC.

Nail circlets are then blotted dry and the thickness measured using a Digimatic Micrometer. Five representative measurements for each nail are taken. Nails are then secured to a wooden dowel using cyanoacrylate adhesive and allowed to fix for a minimum of 30 minutes. Three successive 10 mg nail scrapings are taken from each nail using a single-edge razor blade or Exacto knife. Each scraping is accurately weighed on an analytical balance and placed individually into a 4 ml vial. Ethanol (2 ml of 95%) is added to the vials which are then shaken overnight (orbital shaking, 150–200 rpm). Subsequently, a 100 μl aliquot of the supernatant is added to an HPLC vial containing 900 μPBS to a final 1/10 dilution and analysed by HPLC.

Nails are removed from the dowels and thickness measured by Digimatic Micrometer. The depth of nail scraping is determined by the difference in the thickness of the nails before and after scraping. For porcine nails, the average thickness before scraping (24 nail samples, 5 measurement each) is 1.062±0.134 mm. The average nail thickness after scraping is 0.670±0.138 (corresponding to a nail depth of 0.392±0.14 mm. The weight of each nail scraping ranged between 0.950 to 13.00 mg (first scraping), 9.70 to 14.40 mg (second scraping) and 10.00 to 15.30 mg (third scraping) for an average value of all three scrapings of 33.54±2.02 mg. In contrast, human toe nails (3 samples, 5 measurements) had an average thickness before and after scraping of 0.845±0.022 and 0.385±0.051 mm, respectively. The average weight (total) of the 3 scrapings was 22.23±0.90 mg.

Nail procedure: four multiple applications with wash off between applications

For nails prepared as described immediately above the subsequent dosage regimen is as follows:

Day one: Lacquer, approximately 10 mg, is applied evenly to each nail with an adjustable 50 μl micropipette (VWR) set to 11 μl. Each nail is weighed before and after application of the lacquer and weights are recorded. The exact amount of lacquer applied is determined from the difference in the weight of the nail before and after treatment. Nail circlets are then placed as a group of 4 or 6 (nails 1–6) on the gel and allowed to air dry for 10–15 minutes before covering the dish. The dish is subsequently placed in an incubator set at 40–45° C.

Day two: The day one procedure is repeated with a new group of 4 or 6 nails (7–12). Nails 1–6 are removed from the petri dish and the underside of each nail is rinsed with deionized water to remove adhering gel. Then nails are washed with 2 ml 95% ethanol with orbital shaking as previously described. Samples of the supernatants are stored and the nails treated with fresh lacquer exactly as described for day one. Both sets of nails are placed in the incubator set at 40–45° C.

Days three and four: The day one and day two procedures are repeated with wash-off and re-application, with new groups of 4 or 6 nails (13–18; 19–24).

Day five: All four Petri dishes are removed from the incubator. The nails are removed, rinsed with deionized water, and placed individually into 20 ml vials. Ethanol (2 ml of 95%) is added and the vials are agitated for 15 minutes using an orbital shaker at 150–200 rpm. Supernatants are collected into 4 ml vials. This washing is repeated with 2 ml of fresh ethanol and all of the washing supernatants are combined (collective resultant volumes of washings are 10 ml for nails 1–6; 8 ml for nails 7–12; 6 ml for nails 13–18; 4 ml for nails 19–24). Subsequently, a 50 μl aliquot of the collective washings is added to an HPLC vial containing 950 μl PBS to a final 1/20 dilution and analysed by HPLC. This provides washing recovery data for mass balance determination.

All nail circlets are subsequently treated to determine the levels of econazole in each nail scraping layer, as previously described.

Nail Procedure: four multiple applications without wash off between applications Nails are prepared as described above. The subsequent dosage regimen is as follows:

Day one: Lacquer, approximately 10 mg, is applied evenly to each of 24 nails with an adjustable 50 μl micropipette (VWR) set to 11 μl. Each nail is weighed before and after application of the lacquer and weights are recorded. The exact amount of lacquer applied is determined from the difference in the weight of the nail before and after treatment. Nail circlets are then placed on the gel (as described) and allowed to air dry for 10–15 minutes before covering the dish. The dish is subsequently placed in an incubator set at 40–45° C.

Day two: The Petri dishes are removed from the incubator. Nail samples 1–18 are treated as on day one. The exact amount of lacquer applied is determined by the difference in the weight of the Petri dish before and after application. The dishes are then returned to the incubator. Nail samples 19–24 were removed from the gel, rinsed with deionized water and washed with 95% ethanol. The nails are then scraped according to the procedure described above. Scrapings are stored.

Day three: Lacquer is re-applied to nail samples 1–12. Nail samples 13–18 are removed from the gel, rinsed with deionized water and washed with 95% ethanol. The nails are then scraped according to the procedure described above. Scrapings are stored.

Day four: Lacquer is re-applied to nail samples 1–6. Nail samples 7–12 are removed from the gel, rinsed with deionized water and washed with 95% ethanol. The nails are then scraped according to the procedure described above. Scrapings are stored.

Day five: Nail samples 1–6 are removed from the incubator and treated according to the procedure described above. All washings and scrapings are treated and analysed for econazole as described above.

In Vitro Validation: Human Nail

Human toenails are obtained from a regional organ bank. After debridement and cleaning of the underneath surface, partially hydrated nails are punched out and prepared exactly as described above for porcine nails. The method used for the validation study used "four multiple applications with wash off between applications" method described above.

EXAMPLE 4

Following the general procedure for the single application nail procedure described above the following composition is tested for absorption of Econazole through porcine nail.

| Ingredient | Amount (wt %) |
|---|---|
| Econazole | 5.0 |
| 2-n-Nonyl-1,3-dioxolane | 6.0 |
| Amphomer | 24.0 |
| Ethanol | 65.0 |

In this test, a phosphate buffered saline (PBS): ethanol (95:5) hydroxypropyl cellulose (2%) thickened gel (pH 7.45), is used as a nail support/receptor fluid. 5.6 mg of the formulation is applied (T=40° C.) to 4 nail circlets. Measurement of econazole penetration (avg. for 4 nails) is measured after 48 hours.

The results are shown below in Table 3:

TABLE 3

| Nail Layer | Amount of Econazole (μg/mg) |
|---|---|
| 1 | 1.04 |
| 2 | 0.07 |
| 3 | 0.06 |

This corresponds to a concentration of about 1170 ppm of econazole.

EXAMPLE 5

The procedure of Example 4 is repeated except that the pH of the receptor fluid is increased to 7.7, the amount of lacquer is changed as shown in the following Table 4, and the penetration is measured after 120 hours. The following econazole containing antifungal nail lacquers, as shown in Table 4, are tested by the single application procedure described above.

TABLE 4

| Ingredient | 260A | 260B | 260F |
|---|---|---|---|
| Econazole | 5 | 5 | 20 |
| 2-n-Nonyl-1,3-dioxolane | | 6 | 6 |
| Propylene glycol | 6 | 6 | 6 |
| Dermacryl 79 | 24 | 24 | 24 |
| Ethanol | 65 | 59 | 44 |
| Amt. formulation Applied (mg) | 8.75 | 9.60 | 9.55 |
| Amt. Econazole (μg) | 437.5 | 480.0 | 1910.0 |

The results are shown in the following Table 5 for the average penetration for each layer of the four treated porcine nail circlets.

TABLE 5

| | Amount of Econazole (μg/mg of nail) | | |
|---|---|---|---|
| Sample No. | First Layer | Second Layer | Third Layer |
| 260A | 0.66 | 0.05 | 0.04 |
| 260B | 0.72 | 0.07 | 0.03 |
| 260F | 2.42 | 0.25 | 0.02 |

From these results it is seen that Sample 260B with enhancer was not significantly improved relative to the control Sample 260A and that the penetration of econazole, in Sample 260F, measured as percent of dose was only comparable to Sample 260A and 260B. For subsequent results, it is presumed that the duration of the study (120 hours) was too long, namely, the antifungal agent from Sample 260B substantially completely passed through the nail. In addition, there may have been insufficient fluidization of the antifungal agent.

EXAMPLE 6

In this example the same procedure as described in Example 5 was used except that the test duration is reduced to 96 hours.

The following antifungal lacquer formulations are tested for econazole absorption:

TABLE 6

| Ingredient | 303A | 274A | 274C | 249A |
|---|---|---|---|---|
| Econazole | 5 | 5 | 5 | 5 |
| 2-n-nonyl-1,3-dioxolane | — | 6 | 12 | 6 |
| Propylene Glycol | 6 | 6 | 6 | 6 |
| Eudragit RL | 24 | 24 | 24 | — |
| Dermacryl 79 | — | — | — | 24 |
| Ethanol | 65 | 59 | 53 | 65 |
| Amt. Applied (mg) | 6.98 | 6.83 | 7.98 | 7.58 |
| Drug Amt. (μg) | 348.75 | 341.25 | 398.75 | 378.75 |

The results (average of four porcine nail circlets) are shown in Table 7.

TABLE 7

| | Amount of Econazole (μg/mg) | | |
|---|---|---|---|
| Sample No. | First Layer | Second Layer | Third Layer |
| 303A | 0.7 | 0.18 | 0.15 |
| 274A | 0.72 | 0.22 | 0.15 |
| 274C | 0.74 | 0.18 | 0.12 |
| 249A | 0.34 | 0.16 | 0.13 |

From the results of Table 7 it is seen that the econazole absorption from the Eudragit polymer lacquer is greater than from the Dermacryl polymer lacquer. It is also seen that there is no significant difference between the 6% and 12% enhancer levels, again suggesting the test duration may be overly long.

EXAMPLE 7

This example is another 96 hour test for different concentrations of enhancer in a series of lacquer formulations containing 5% econazole and 24% Eudragit RL. The amount (wt %) of enhancer (2-n-nonyl-1,3-dioxolane) and alcohol in each formulation is shown below.

| Sample No. | Enhancer:Ethanol |
|---|---|
| 318A | 0:71 |
| 318C | 5:66 |
| 318D | 12:59 |
| 318E | 18:53 |
| 318F | 24:47 |

The procedure used is the same as described in Example 5 except that the receptor fluid (gel support) is 90% PBS/10% PEG 200, pH 4.8. The amount of lacquer applied in this series of runs varied between 6.38 mg to 7.65 mg.

The results are shown in Table 8.

TABLE 8

| | Amount of Econazole (μg/mg) | | |
|---|---|---|---|
| Sample No. | First Layer | Second Layer | Third Layer |
| 318A | 0.75 | 0.14 | 0.03 |
| 318C | 0.64 | 0.16 | 0.08 |
| 318D | 0.56 | 0.07 | 0 |
| 318E | 0.5 | 0 | 0.05 |
| 318F | 0.45 | 0.09 | 0.07 |

Based on the inverse correlation of enhancer concentration and antifungal agent absorption it is concluded that the study duration (96 hours) is too long, namely the antifungal agent has already substantially passed through the nail thickness.

Accordingly, the same procedure as above is reported but for a test duration of only 48 hours and using 6 porcine nail circlets. Also, the amount of lacquer applied was slightly increased, on average, ranging from 7.10 mg to 8.52 mg. The results are shown in Table 9.

TABLE 9

| Amount of Econazole (μg/mg) | | | | |
|---|---|---|---|---|
| Sample No. | First Layer | Second Layer | Third Layer | Total |
| 318A | 0.52 | 0.06 | 0 | 0.58 |
| 318C | 0.41 | 0.13 | 0.02 | 0.56 |
| 318D | 0.56 | 0.08 | 0.08 | 0.72 |
| 318E | 0.79 | 0.09 | 0.03 | 0.91 |

Based on the control sample (318A, 0% SEPA) the change in enhancement is as follows: (the amount of SEPA is shown in parentheses).

| | % Enhancement vs. Control |
|---|---|
| 318C (5%) vs. 318A (0%) | −6% |
| 318D (12%) vs. 318A (0%) | +23% |
| 318E (18%) vs. 318A (0%) | +56% |

To further determine the effect of test duration on the same sample formulations (separately prepared) as used above with 0, 12, 18 and 24% SEPA, the same procedure described above is again carried out but only for a 24 hour period. The results are shown in Table 10.

TABLE 10

| Ingredient | 338A | 338B | 338C | 338D |
|---|---|---|---|---|
| Econazole | 5 | 5 | 5 | 5 |
| Enhancer | — | 12 | 18 | 24 |
| Eudragit RL | 24 | 24 | 24 | 24 |
| Ethanol | 71 | 59 | 53 | 47 |
| Amount Econazole Absorbed (μg/mg) | | | | |
| First Layer | 0.91 | 1.2 | 0.75 | 0.84 |
| Second Layer | 0.14 | 0.11 | 0.09 | 0.08 |
| Third Layer | 0.06 | 0.16 | 0.08 | 0.08 |
| Total (ppm) | 1102 | 1462 | 943 | 1006 |
| Enhancement vs. Control | — | +33% | −14% | −9% |

While this example shows significant enhancement using 12% concentration of enhancer (2-n-nonyl-1,3-dioxolane), based on other tests, as described below, it is concluded that the 24 hour test duration for the single application is too short.

EXAMPLE 8

This example is designed to show the effect of various excipients.

Using the same single application procedure as described in Example 7 except that the test duration is 48 hours, the following four samples were compared:

TABLE 11

| Ingredient | 353A | 353B | 353C | 353D |
|---|---|---|---|---|
| Econazole | 5 | 5 | 5 | 5 |
| Eudragit RL | 24 | 24 | 24 | 24 |
| 2-n-nonyl-1,3-dioxolane | 18 | 18 | 18 | 18 |
| Propylene Glycol | — | 6 | — | — |
| Triacetin | — | — | 6 | — |
| Citroflex* | — | — | — | 6 |
| Ethanol | 53 | 47 | 47 | 47 |

*acylated triesters of citric acid (Morflex, Inc.) The results are shown in Table 12.

TABLE 12

| Econazole, Amount (μg/mg) | | | | |
|---|---|---|---|---|
| Sample No. | First Layer | Second Layer | Third Layer | Total |
| 353A | 1.36 | 0.17 | 0 | 1.534 |
| 353B | 1.76 | 0.35 | 0.07 | 2.176 |
| 353C | 1.15 | 0.08 | 0.07 | 1.304 |
| 353D | 0.49 | 0.07 | 0.09 | 0.647 |

EXAMPLE 9

This example is designed to show the effect of increasing the concentration of antifungal agent for a single dose application under the same conditions described in Example 7. The following lacquer samples are prepared.

| Ingredient | 353-B | 357-B | 357-C | 357-D |
|---|---|---|---|---|
| Econazole | 5 | 5 | 10 | 20 |
| Eudragit RL | 24 | 24 | 24 | 24 |
| 2-n-nonyl-1,3-dioxolane | 18 | 18 | 18 | 18 |
| Propylene Glycol | 6 | — | — | — |
| Ethanol | 47 | 53 | 48 | 38 |

The results for absorption of econazole in each nail layer (average of six nails) is shown in Table 13.

TABLE 13

| Amount Econazole Absorbed (μg/mg) (48 h) | | | | |
|---|---|---|---|---|
| Sample No. | First Layer | Second Layer | Third Layer | Total |
| 353B | 1.61 | 0.06 | 0.09 | 1.769 |
| 357B | 1.23 | 0.07 | 0.09 | 1.392 |
| 357C | 1.87 | 0.09 | 0.02 | 1.984 |
| 357D | 1.51 | 0.15 | 0.01 | 1.675 |

These results suggest that no significant benefit is achieved by increasing the dose of antifungal agent from 10% to 20%.

In order to test the effect of antifungal agent doses below 5% the following antifungal nail lacquers were prepared and tested by the same procedure as above. The formulations of each sample and the results are shown in Table 14.

TABLE 14

| Ingredient | 906A | 906B | 906C | 906D |
|---|---|---|---|---|
| Econazole | 1 | 2 | 5 | 10 |
| Eudragit RL | 24 | 24 | 24 | 24 |

TABLE 14-continued

| Ingredient | 906A | 906B | 906C | 906D |
|---|---|---|---|---|
| 2-n-nonyl-1,3-dioxolane | 18 | 18 | 18 | 18 |
| Ethanol | 57 | 56 | 53 | 48 |
| Amount Econazole Absorbed (μg/mg) (48h) | | | | |
| First Layer | 0.31 | 0.49 | 0.76 | 1.09 |
| Second Layer | 0.45 | 0.17 | 0.15 | 0.3 |
| Third Layer | 0.22 | 0.27 | 0.16 | 0.77 |
| Total | 0.986 | 0.920 | 1.067 | 2.166 |

EXAMPLE 10

This and the following examples are designed to show the effect of multiple lacquer applications. In this example the test procedure for multiple applications with washoff (using ethanol) as described above is applied to six porcine nail circlets using as the nail support/receptor fluid PBS:PEG200 (90:10) (pH, 5.13), and the following nail lacquer:

| | |
|---|---|
| Econazole | 5% |
| Eudragit RL | 24% |
| 2-n-nonyl-1,3-dioxolane | 18% |
| Propylene Glycol | 6% |
| Ethanol | 47% |

The results are shown in Table 15.

TABLE 15

| | Amount of Econazole (μg/ml) | | | |
|---|---|---|---|---|
| Application | First Layer | Second Layer | Third Layer | Total |
| 1 | 1.25 | 0.25 | 0.2 | 1.693 |
| 2 | 1.64 | 0.42 | 0.16 | 2.228 |
| 3 | 2.37 | 0.78 | 0.21 | 3.365 |
| 4 | 2.69 | 0.58 | 0.38 | 3.654 |

From Table 15 is it seen that there is a significant dose response with multiple daily applications, however, steady state appears to occur after the third application.

EXAMPLE 11

This example shows the effects of multiple (once daily) applications similarly to Example 10 but without washing between applications. In this example, the nail lacquer was similar to that used in Example 10, except that propylene glycol is not used, and is replaced with an equivalent amount of ethanol, namely, 5% econazole, 24% Eudragit RL, 18% enhancer (2-n-nonyl-1,3-dioxolane) and 53% ethanol.

The results are reported in Table 16.

TABLE 16

| | Amount of Econazole (μg/mg) | | | |
|---|---|---|---|---|
| Application | First Layer | Second Layer | Third Layer | Total |
| 1 | 0.69 | 0.12 | 0.27 | 1.157 |
| 2 | 1.57 | 0.34 | 0.22 | 2.135 |
| 3 | 1.4 | 0.29 | 0.29 | 1.986 |
| 4 | 2.32 | 0.71 | 0.47 | 3.493 |

As compared to Example 10 where the lacquer is removed by washing between applications, it is seen that without washing the dose response curve achieves a statistically significant maximum after the fourth application.

EXAMPLE 12

This example is similar to Example 10 (wash off after each 24 hour application) using the same antifungal nail lacquer used in Example 10. The results are shown in Table 17.

TABLE 17

| | Amount of Econazole (μg/mg) | | | |
|---|---|---|---|---|
| Application | First Layer | Second Layer | Third Layer | Total |
| 1 | 0.53 | 0.34 | 0.61 | 1.492 |
| 2 | 0.48 | 0.53 | 0.61 | 1.625 |
| 3 | 0.81 | 0.57 | 0.61 | 1.983 |
| 4 | 1.03 | 0.84 | 0.75 | 2.620 |

EXAMPLE 13

This example is similar to Example 12 (four daily applications without washoff between applications) but using the same antifungal nail lacquer as used in Example 7, Sample 353B. The results are shown in Table 18.

TABLE 18

| | Amount of Econazole (μg/mg) | | | |
|---|---|---|---|---|
| Application | First Layer | Second Layer | Third Layer | Total |
| 1 (24 h) | 1.36 | 0.17 | 0 | 1.534 |
| 2 (48 h) | 1.76 | 0.35 | 0.07 | 2.176 |
| 3 (72 h) | 1.15 | 0.08 | 0.07 | 1.304 |
| 4 (96 h) | 0.49 | 0.07 | 0.09 | 0.647 |

EXAMPLE 14

This example is designed to compare the effects of several enhancers according to this invention.

Using the same procedures as described in Example 8, the following antifungal nail lacquers are tested for econazole absorption after 48 hours.

TABLE 18

| Ingredient | 911-A | 911-B | 911-C | 911-D |
|---|---|---|---|---|
| Eudragit RL | 24 | 24 | 24 | 24 |
| Enhancer: | | | | |
| 2-n-nonyl-1,3-dioxolane | 18 | — | — | — |
| 2,6-dimethyl-2,7-heptadienyl-1,3-dioxolane | — | 18 | — | — |
| 2-n-heptyl-1,3-dioxolane | — | — | 18 | — |
| decanal dimethyl acetal | — | — | — | 18 |
| Ethanol | 53 | 53 | 53 | 53 |

The results are shown in Table 19.

TABLE 19

| | Econazole Absorption (48 h) (μg/mg) | | | |
|---|---|---|---|---|
| Sample No. | First Layer | Second Layer | Third Layer | Total |
| 911-A | 1.03 | 0.05 | 0.02 | 1.115 |
| 911-B | 0.78 | 0.01 | 0 | 0.79i |
| 911-C | 0.78 | 0.05 | 0.03 | 0.85S |
| 911-D | 0.76 | 0.01 | 0.05 | 0.813 |

EXAMPLE 15

This is an in vitro validation study using human toenail specimens in a procedure similar to that described above using four consecutive daily applications of the test sample with wash off between applications, except that the PBS/PEG200 support gel is replaced by a PBS/Ethanol (80:20) gel (pH, 7.7). The same formulation as used in Example 10 (separately prepared) is used in this example. The results after the fourth application (96 hours) are shown in Table 20, as the average of six replicates.

TABLE 20

| Amount of Econazole (μg/mg) | |
|---|---|
| Layer 1 | 0.82 |
| Layer 2 | 0.90 |
| Layer 3 | 1.49 |
| Total | 3.210 |

EXAMPLE 16

This example shows the percutaneous absorption of econazole through human skin using lacquer compositions with or without the skin penetration enhancing compound.

In a first series of experiments conducted for 96 hours using the static cell method (receptor fluid PBS/ethanol (80:20), pH 7.7, temperature 32° C.) the following lacquer formulations were tested to determine the effect on percutaneous absorption of antifungal agent (econazole, 5%) of enhancer (2-n-nonyl-1,3-dioxolane, 0%, 6% or 12%) and various polymeric film-formers, as follows:

TABLE 21

| | Sample No. (wt. %) | | | | | | | |
|---|---|---|---|---|---|---|---|---|
| Ingredient | 303-A | 274-D | 274A | 274C | 249A | 249B | 242C | 242A |
| Econazole | 5 | 5 | 5 | 5 | 5 | 5 | 5 | 5 |
| Enhancer | 0 | 6 | 6 | 12 | 6 | 6 | 12 | 12 |
| Propylene Glycol | 6 | 0 | 6 | 6 | 0 | 6 | 0 | 6 |
| Eudragit RL | 24 | 24 | 24 | 24 | — | — | — | — |
| Dermacryl 79 | — | — | — | — | 24 | 24 | — | — |
| Amphomer LV71 | — | — | — | — | — | — | 24 | 24 |
| Ethanol | 65 | 65 | 59 | 53 | 65 | 65 | 59 | 59 |

The results are shown in the following Table 22 (average (for 6 or 5 replicates) cumulative (96 h) percutaneous absorption through the skin, i.e., amount in receptor) as well as in the epidermis and dermis); Table 23 (cumulative (96 h) delivery of antifungal agent as percent of dose for receptor, epidermis and dermis).

TABLE 22

| Sample No. | Receptor Amt. (μg) | Epidermis (μg) | Dermis (μg) |
|---|---|---|---|
| 303-A (n = 6) | 1.58 ± 0.78 | 2.13 ± 2.42 | 0.83 ± 1.48 |
| 274-D (n = 5) | 5.59 ± 0.75 | 6.08 ± 2.14 | 1.82 ± 1.21 |
| 274-A (n = 6) | 7.06 ± 1.25 | 9.14 ± 3.43 | 2.37 ± 1.67 |
| 274-C (n = 6) | 13.25 ± 2.20 | 13.50 ± 6.61 | 6.09 ± 1.90 |
| 249-A (n = 6) | 1.74 ± 0.88 | 9.76 ± 4.05 | 1.34 ± 1.17 |
| 249-B (n = 6) | 1.58 ± 0.71 | 9.30 ± 6.70 | 0.96 ± 1.29 |
| 242-C (n = 6) | 3.25 ± 0.45 | 11.83 ± 7.31 | 2.17 ± 1.19 |
| 242-A (n = 5) | 3.64 ± 0.41 | 9.14 ± 3.10 | 2.63 ± 0.70 |

TABLE 23

| Sample No. | Receptor | Epidermis | Dermis |
|---|---|---|---|
| 303-A | 0.31 ± 0.18 | 0.40 ± 0.46 | 0.17 ± 0.31 |
| 274-D | 1.07 ± 0.26 | 1.13 ± 0.38 | 0.33 ± 0.21 |
| 274-A | 1.43 ± 0.31 | 1.83 ± 0.67 | 0.48 ± 0.35 |
| 274-C | 2.51 ± 0.50 | 2.52 ± 1.17 | 1.15 ± 0.35 |
| 249-A | 0.39 ± 0.18 | 2.17 ± 0.81 | 0.30 ± 0.27 |
| 249-B | 0.31 ± 0.14 | 1.92 ± 1.27 | 0.20 ± 0.27 |
| 242-C | 0.66 ± 0.14 | 2.24 ± 1.17 | 0.42 ± 0.23 |
| 242-A | 0.78 ± 0.06 | 1.91 ± 0.59 | 0.55 ± 0.16 |

What we claim is:

1. A composition effective for the treatment or prevention of fungal infections of nails, comprising:

(a) at least one antifungal agent effective in the treatment or prevention of onychomycoses;

(b) a penetration enhancing agent selected from the group consisting of $C_7$–$C_{14}$-hydrocarbyl substituted 1,3-dioxolane, $C_7$–$C_{14}$-hydrocarbyl substituted 1,3-dioxane and $C_7$–$C_{14}$-substituted acetal;

(c) water-insoluble, film-forming polymer; and, (d) volatile solvent;

the composition, when applied to nails, forming, upon evaporation of the volatile solvent, a hard, water-resistant film from which the antifungal agent is releasable and becomes available to treat or prevent fungal infection.

2. The composition of claim 1 wherein the antifungal agent is selected from the group consisting of polyenes, allylamines, imidazoles, triazoles, ciclopirox, undecylenic acid, and amorolfine.

3. The composition of claim 1 wherein the antifungal agent comprises at least one of amorolfine, ciclopirox and econazole.

4. The composition of claim 1 wherein the antifungal agent comprises ciclopirox.

5. The composition of claim 1 wherein the antifungal agent comprises econazole.

6. The composition of claim 1 which further comprises antiinflammatory effective amount of steroidal antiinflammatory agent.

7. The composition of claim 6 wherein the steroidal antiinflammatory agent comprises at least one of hydrocortisone, triamcinolone, betamethasone, or clobestol or the salts thereof.

8. The composition of claim 1 which further comprises a plasticizer for the film-forming polymer.

9. The composition of claim 8 wherein the plasticizer is at least one plasticizer selected from the group consisting of glycols, glycol esters, phthalate esters, citrate esters, polyethylene glycols, dipropyleneglycol and polypropylene glycols.

10. The composition of claim 1 wherein the film-forming polymer comprises a water-insoluble film-forming polymer selected from the group consisting of acrylate polymers, methacrylate polymers, and copolymers of alkyl vinyl ether and maleic anhydride.

11. The composition of claim 1 wherein the film-forming polymer comprises an acrylic copolymer.

12. The composition of claim 11 wherein the acrylic copolymer comprises recurring units of at least one of the following moieties (IV) and (V):

(IV)

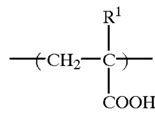

(V)

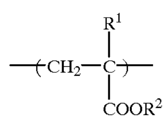

wherein $R^1$ represents H or $CH_3$; and $R^2$ represents an alkyl group.

13. The composition of claim 11 wherein the acrylic copolymer comprises recurring units of the moiety (V) and wherein $R^2$ is an alkyl of at least 4 carbon atoms.

14. The composition of claim 11 wherein the acrylic copolymer comprises recurring units of a moiety of formula (VI)

(VI)

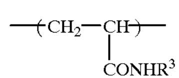

wherein $R^3$ represents an alkyl group.

15. The composition of claim 11 wherein the acrylic copolymer comprises recurring units of formula (V) or formula (VI) or both formulas (V) and (VI), and, optionally, recurring units of formula (IV):

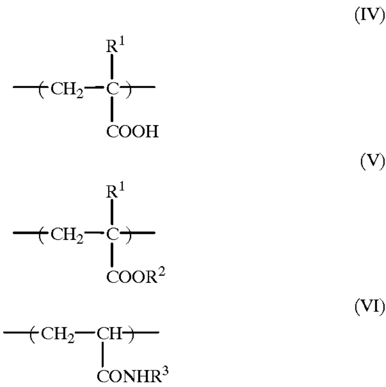

wherein R represents H or $CH_3$; $R^2$ represents an alkyl group, and $R^3$ represents an alkyl group; at least one of $R^2$ and $R^3$ representing an alkyl group having at least 4 carbon atoms.

16. The composition of claim 11 wherein the acrylic copolymer comprises recurring units of a moiety containing a cationic amine group.

17. The composition of claim 16 wherein the cationic amine group is carboethoxy-t-butyl amine.

18. The composition of claim 1 wherein the water-insoluble, film-forming polymer comprises a copolymer of methyl vinyl ether or ethyl vinyl ether and at least one comonomer of formula (VII):

(VII)

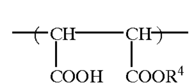

wherein $R^4$ represents a lower alkyl group.

19. The composition of claim 18 wherein said copolymer comprises recurring units of formula (VII) wherein $R^2$ is an alkyl group of at least 2 carbon atoms.

20. The composition of claim 1 wherein the volatile solvent is selected from the group consisting of lower alkanols, lower alkyl esters of lower carboxylic acids, lower alkyl ethers, lower alkyl ketones, and mixtures thereof.

21. The composition of claim 1 wherein the penetration enhancer is 2-n-nonyl-1,3-dioxolane, decanal diethylacetal or decanal dimethylacetal.

22. The composition of claim 1 which comprises:

(a) at least one antifungal agent selected from the group consisting of amorolfine, ciclopirox and econazole;

(b) a penetration enhancing agent selected from the group consisting of 2-n-nonyl-1,3-dioxolane, decanal diethylacetal and decanal dimethylacetal;

(c) water-insoluble, film-forming polymer selected from the group consisting of (meth)acrylate copolymer and alkyl vinyl ether copolymer;

(d) volatile solvent selected from the group consisting of ethanol, n-propanol, isopropanol, n-butanol, isobutanol, acetone, ethyl acetate, propyl acetate, n-butyl acetate, n-amyl acetate, methyl ether, methylethyl ether, methylethyl ketone, methylene chloride, methyl chloroform, toluene, tetrahydrofuran, 1,4-dioxane, and mixtures thereof;

(e) plasticizer for the film-forming copolymer selected from the group consisting of glycols, glycol esters, phthalate esters, citrate esters, polyethylene glycol, dipropylene glycol, polypropylene glycols, and mixtures thereof.

23. The composition of claim 1 which comprises:

from about 0.5 to about 20 percent (a) antifungal agent;

from about 0.5 to about 35 percent (b) penetration enhancing agent;

from about 0.5 to about 40 percent (c) film-forming polymer; and from about 10 to about 70 percent (d) volatile solvent.

24. The composition of claim 23 which further comprises from about 0.5 to about 20 percent (e) plasticizer for the film-forming copolymer.

25. A method for the treatment of a fungal infection which comprises applying to an infected nail a nail lacquer composition as defined in claim 1.

26. A method for preventing a fungal infection from developing which comprises applying to the nail of a person in need thereof a nail lacquer composition as defined in claim 1.

27. A nail lacquer composition effective for applying a water-resistant adherent film to animal nails, comprising a substantially non-aqueous solution of water-resistant, film-forming polymer, and plasticizing effective amount of at least one compound selected from the group consisting of $C_7$–$C_{14}$-hydrocarbyl substituted 1,3-dioxolane, $C_7$–$C_{14}$-hydrocarbyl substituted 1,3-dioxane and $C_7$–$C_{14}$-substituted acetal in volatile solvent.

28. The nail lacquer composition of claim 27 further comprising in said solution at least one additional plasticizer for the water-resistant film-forming polymer.

29. An antifungal nail lacquer composition comprising a substantially non-aqueous solution of water-resistant, film-forming polymer, antifungal agent effective in the treatment or prevention of onychomycoses, and steroidal antiinflammatory agent in volatile solvent.

30. A plasticized film-forming composition comprising water-insoluble film-forming polymer, and plasticizing effective amount of a compound selected from the group consisting of $C_7$–$C_{14}$ hydrocarbyl substituted 1,3-dioxolane, $C_7$–$C_{14}$-hydrocarbyl substituted 1,3-dioxolane and $C_7$–$C_{14}$ hydrocarbyl substituted acetal.

31. The composition of claim 1, wherein the amount of said penetration enhancing agent is from about 3 to about 30 percent, by weight, of the total composition.

32. The composition of claim 1, wherein the amount of said penetration enhancing agent is from about 5 to about 25 percent, by weight, based on the total composition.

33. The composition of claim 1, wherein the penetration enhancing agent is present in an amount of from about 12 to about 24% by weight, based on the total composition, said amount of penetration enhancing agent acting as a plasticizer for said film-forming polymer, said composition not including another plasticizer.

34. The composition of claim 33, wherein the amount of the penetration enhancing agent is from about 15 to about 20% by weight, based on the total composition.

35. The composition of claim 1, wherein the film-forming polymer and the penetration enhancing agent are present in the composition at a weight ratio of polymer to agent of from about 4:1 to about 1:1.

36. The composition of claim 35, wherein said weight ratio is from about 3:1 to about 1.2:1.

37. The composition of claim 35, wherein said weight ratio is from about 2:1 to about 1.2:1.

38. The composition of claim 1, which comprises:

from about 1 to about 10% by weight of (a) antifungal agent;

from about 5 to about 25% by weight of (b) penetration enhancing agent;

from about 15 to about 50% by weight of (c) film-forming polymer; and, (d) solvent, balance.

39. The composition according to claim 1, wherein the weight ratio of (c) film-forming polymer to (b) penetration enhancing agent (b) is from about 4:1 to about 1:1.

40. The composition according to claim 39, wherein said weight ratio of (b):(c) is from about 3:1 to about 1.2:1.

* * * * *

UNITED STATES PATENT AND TRADEMARK OFFICE

CERTIFICATE OF CORRECTION

PATENT NO. : 6,224,887 B1
DATED : May 1, 2001
INVENTOR(S) : Carlos M. Samour et al.

It is certified that error appears in the above-identified patent and that said Letters Patent is hereby corrected as shown below:

Column 32,
Line 39, "(b):(c)" should read -- (c):(b) --.

Signed and Sealed this

Second Day of August, 2005

JON W. DUDAS
*Director of the United States Patent and Trademark Office*